(12) United States Patent
Hickmott et al.

(10) Patent No.: US 11,534,327 B2
(45) Date of Patent: Dec. 27, 2022

(54) COMPLEMENTARY-MATERIAL ELEMENT FOR AN OSTOMY APPLIANCE

(71) Applicant: Coloplast A/S, Humlebaek (DK)

(72) Inventors: Richard Morgan Hickmott, Helsingoer (DK); Philip Holler Langhorn, Hilleroed (DK); Kristoffer Hansen, Naerum (DK); Joergen Daucke von Barner, Struer (DK); Anders Grove Sund, Alleroed (DK)

(73) Assignee: Coloplast A/S, Humlebaek (DK)

( * ) Notice: Subject to any disclaimer, the term of this patent is extended or adjusted under 35 U.S.C. 154(b) by 248 days.

(21) Appl. No.: 16/761,816

(22) PCT Filed: Nov. 2, 2018

(86) PCT No.: PCT/DK2018/050279
§ 371 (c)(1),
(2) Date: May 6, 2020

(87) PCT Pub. No.: WO2019/091527
PCT Pub. Date: May 16, 2019

(65) Prior Publication Data
US 2021/0186741 A1   Jun. 24, 2021

(30) Foreign Application Priority Data
Nov. 8, 2017  (DK) .......................... PA 2017 70836

(51) Int. Cl.
*A61F 5/443*     (2006.01)
*A61F 5/44*      (2006.01)
(Continued)

(52) U.S. Cl.
CPC ............ *A61F 5/443* (2013.01); *A61F 5/4404* (2013.01); *A61F 5/455* (2013.01); *B32B 5/18* (2013.01);
(Continued)

(58) Field of Classification Search
CPC ........ A61F 5/443; A61F 5/4044; A61F 5/455; A61F 5/448; A61F 5/44; B32B 5/18;
(Continued)

(56) References Cited

U.S. PATENT DOCUMENTS

| 1,256,866 A | 2/1918 | Bender |
| 3,302,647 A | 2/1967 | Marsan |

(Continued)

FOREIGN PATENT DOCUMENTS

| EP | 2527823 A1 | 11/2012 |
| GB | 2422112 A  | 7/2006  |

(Continued)

*Primary Examiner* — Tatyana Zalukaeva
*Assistant Examiner* — Hans Kaliher
(74) *Attorney, Agent, or Firm* — Coloplast Corp., Coloplast A/S; Nick Baumann

(57) ABSTRACT

A complementary-material element configured to be attachable to a base plate of an ostomy appliance and comprising a release layer, the element comprising a release layer comprises a neutralizing component configured to be releasable from the complementary-material element in response to subjection of the complementary-material element to moisture. The complementary-material element comprises a first surface and a second surface, wherein the first surface is provided with a first cover layer.

15 Claims, 5 Drawing Sheets

(51) Int. Cl.
*B32B 5/18* (2006.01)
*B32B 7/06* (2019.01)
*B32B 7/12* (2006.01)
*A61F 5/455* (2006.01)

(52) U.S. Cl.
CPC ............... *B32B 7/06* (2013.01); *B32B 7/12* (2013.01); *B32B 2307/412* (2013.01); *B32B 2307/726* (2013.01); *B32B 2307/748* (2013.01)

(58) Field of Classification Search
CPC ....... B32B 7/06; B32B 7/12; B32B 2307/412; B32B 2307/726; B32B 2307/748
See application file for complete search history.

(56) References Cited

U.S. PATENT DOCUMENTS

| | | | | |
|---|---|---|---|---|
| 3,908,658 A | * | 9/1975 | Marsan | A61L 24/043 604/336 |
| 5,496,296 A | * | 3/1996 | Holmberg | A61F 5/443 604/336 |
| 7,862,878 B2 | * | 1/2011 | Stroebech | A61F 5/443 428/137 |
| 2003/0171737 A1 | * | 9/2003 | Leise, Jr. | A61F 5/448 264/40.1 |
| 2007/0282284 A1 | * | 12/2007 | Mullejans | A61F 5/441 604/333 |
| 2009/0312685 A1 | * | 12/2009 | Olsen | A61F 13/0269 604/386 |
| 2010/0114044 A1 | * | 5/2010 | Cramer | A61F 5/448 604/332 |

FOREIGN PATENT DOCUMENTS

| | | |
|---|---|---|
| GB | 2534012 A1 | 7/2016 |
| NO | 2007092289 A2 | 8/2007 |
| WO | 2017190752 A1 | 11/2017 |
| WO | 2018188705 A1 | 10/2018 |
| WO | 2018188706 A1 | 10/2018 |
| WO | 2018188707 A1 | 10/2018 |

\* cited by examiner

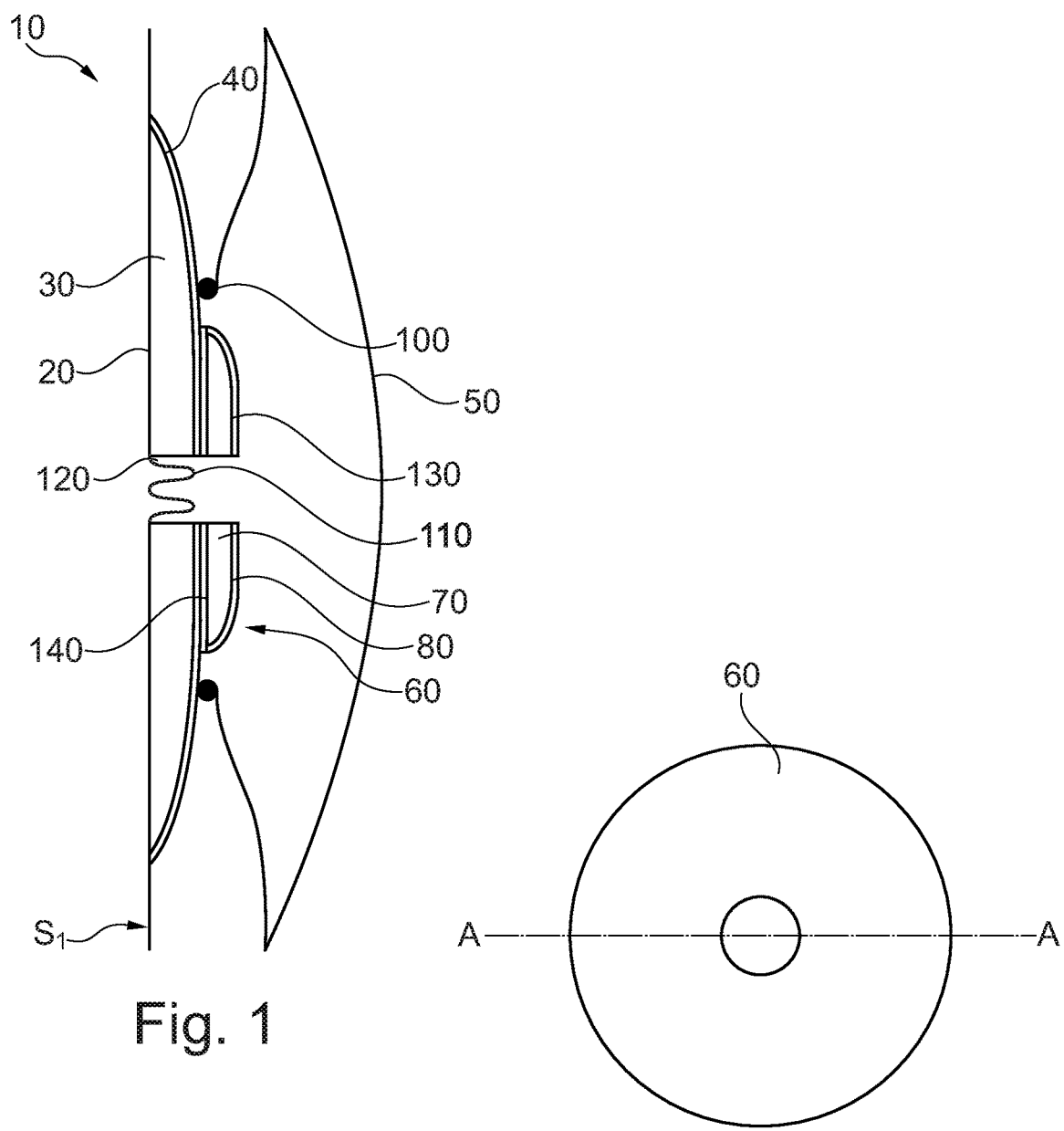
Fig. 1
Fig. 2
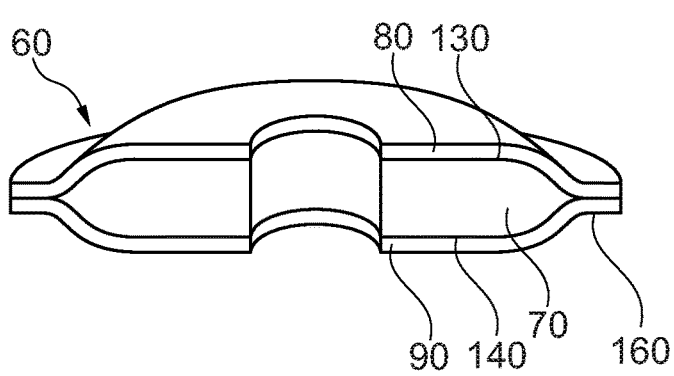
Fig. 3

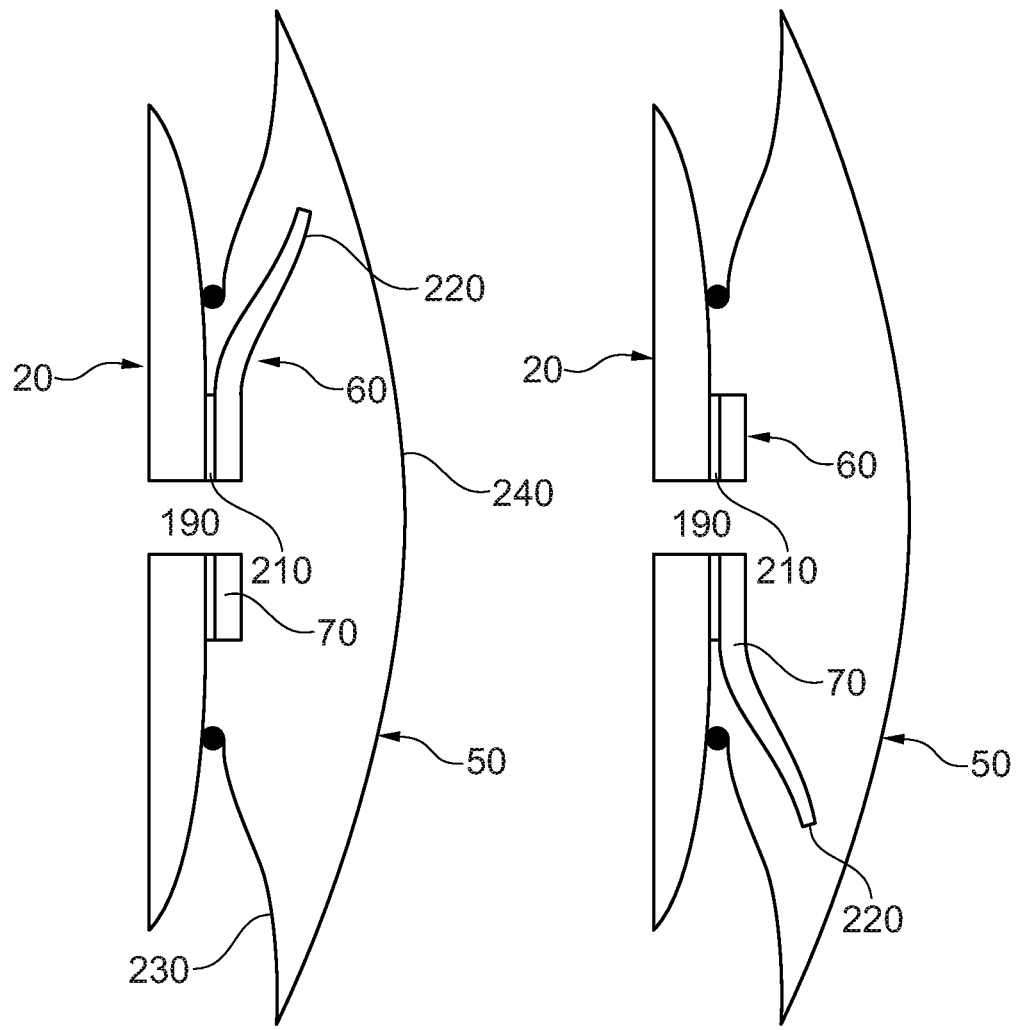

COMPLEMENTARY-MATERIAL ELEMENT FOR AN OSTOMY APPLIANCE

The invention relates to a complementary-material element for an ostomy appliance and a kit of parts.

SUMMARY

The present disclosure provides aspects of a complementary-material element configured to be attachable to a base plate of an ostomy appliance. The complementary-material element is defined and characterized by the appended claims.

BACKGROUND

Stomal output often contains body fluids and visceral contents that are aggressive to both the skin of a user and to ostomy devices, in particular these have a detrimental effect on the efficiency and integrity of the adhesive materials that are applied to attach the ostomy device to the user's skin surface. Some ostomists may choose or have to wear their device for prolonged periods of time. For users in general, and particularly for these ostomists safe, reliable and efficient ostomy devices are highly desirable. Furthermore, a device that protects the skin of the user against the aggressive contents of the stomal output is desired.

Numerous attempts have been made to provide ostomy devices to meet the such demands, e.g. the demand of prolonged wear time and/or higher skin protection, but the provision of sufficient efficiency to achieve a satisfactory long wear time of ostomy devices or skin protection continues to be an unmet need. Ostomists (ostomy appliance users) and health care professionals alike would welcome improvements in ostomy devices to better meet such demands.

BRIEF DESCRIPTION OF THE DRAWING

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1 is a schematic, cross-sectional view of one embodiment of a body side member of an ostomy appliance.

FIG. 2 is a top view of an embodiment of a complementary-material element.

FIG. 3 is a schematic cross-sectional perspective view of an embodiment of a complementary-material element.

FIG. 9 is a cross-sectional view of an embodiment of an appliance with a asymmetric complementary-material element extending further upwards.

FIG. 10 is a cross-sectional view of an embodiment of an appliance with a asymmetric complementary-material element extending further downwards.

DETAILED DESCRIPTION

Figure 4:
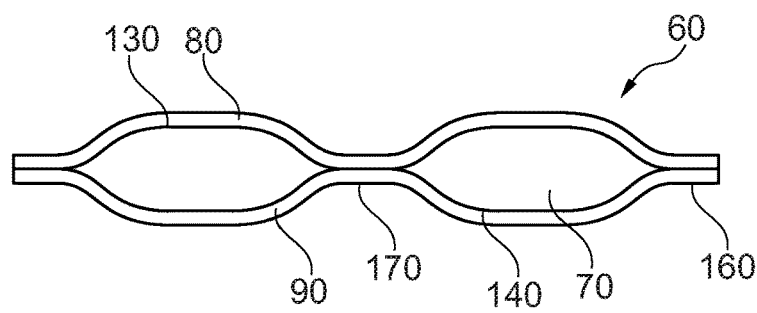
FIG. 4 is a schematic cross-sectional view of an embodiment of a complementary-material element with sealed edges.

In the following Detailed Description, reference is made to the accompanying drawings, which form a part hereof, and in which is shown by way of illustration specific embodiments in which the invention may be practiced. In this regard, directional terminology, such as "top", "bottom", "front", "back", "leading", "trailing" etc., is used with reference to the orientation of the Figure(s) being described. Because components of embodiments can be positioned in a number of different orientations, the directional terminology is used for purposes of illustration and is in no way limiting. It is to be understood that other embodiments may be utilized, and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc. Also, the solid and liquid wastes emanating from the stoma may be referred to as both stomal "output," "waste(s)," and "fluids" interchangeably.

By (stomal) output is herein meant the effluent from a stoma, being feces and/or urine in a more or less viscous form and/or mucins secreted from the epithelial layer of the alimentary canal. In the case of a colostomy, the output may be quite solid, whereas an ileostomy may produce more liquid output. The output may contain digestive fluids with enzymes and other components that may be aggressive to the skin and thus may cause maceration and contact dermatitis of the skin if brought into contact with it as well as the output may comprise components that may attack and degrade the adhesive.

A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side of a device or part of a device, the referral is to the skin-facing side, when the ostomy appliance is worn by a user. Likewise, whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction is defined as the direction of the stoma, when the appliance is worn by a user. Thus, the axial direction is generally perpendicular to the skin or abdominal surface of the user.

The radial direction is defined as transverse to the axial direction that is transversely to the direction of the stoma. In some sentences, the words "inner" and "outer" may be used. These qualifiers should generally be perceived with reference to the radial direction, such that a reference to an "outer" element means that the element is farther away from a centre portion of the ostomy appliance than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the phrase "substantially" as a qualifier to certain features or effects in this disclosure is intended to simply mean that any deviations are within tolerances that would normally be expected by the skilled person in the relevant field.

In one aspect, the present disclosure relates to a complementary-material element configured to be attachable to a base plate of an ostomy appliance and comprising a release layer, wherein the release layer comprises a neutralizing component configured to be releasable from the complementary-material element in response to subjection of the complementary-material element to moisture, wherein the complementary-material element comprises a first surface and a second surface, wherein the first surface is provided with a first cover layer.

The complementary-material element (in the following designated 'CME') is to be understood as an element which is separate from and attachable to a base plate of an ostomy appliance. The wording 'base plate' is commonly used within the technical field of ostomy appliances and the skilled person is familiar with this term. The term 'base plate' is used for that element or part of an ostomy appliance which attaches the appliance to a skin surface around a user's stoma, most commonly by an adhesive interface. Thus, it is the intention of the terminology 'CME' used in this disclosure to mean an element which is not a base plate of an ostomy appliance, but which itself is a 'stand-alone' element. The 'CME' is configured to be attached to a base plate of an ostomy appliance, but is otherwise an individual, or distinct, element.

Particularly, the release layer of the 'CME' includes a neutralizing component. The neutralizing component is configured to be released from the 'CME' in response to subjection of the 'CME' to moisture. Thus, when the 'CME' is attached to (used with) a base plate of an ostomy appliance being worn by a user, the moisture content of the stomal output will act to initiate, sustain and/or accelerate release of the neutralizing component from the 'CME'. Suitable materials for the neutralizing component are discussed below.

When an ostomy appliance is applied to the skin surrounding a stoma, adhesive on the base plate ideally provides a tight fit or sealing to the skin, to avoid stomal output from propagating under the adhesive of the base plate, which is potentially damaging to the skin and prone to degrading the adhesive as explained above. Any stomal output propagating or seeping under the adhesive of base plate is to be avoided as best as possible as such output can lead to maceration of the skin, contact dermatitis and degradation of the adhesive, potentially resulting in adhesive failure and eventually leakage of the stomal output onto the user's clothes, presenting a stigmatising embarrassment and clearly discomfort to the user. However, experience has shown that avoiding any or all kind of such problems is extremely difficult and that users regularly are faced with these issues.

According the disclosure, such adhesive failures can be overcome in that the neutralizing composition included in the release layer of the 'CME' is configured to be released in the presence of moisture and thereby act to neutralize the aggressive contents of the stomal output to help avoid or reduce maceration of the skin, contact dermatitis and/or degradation of the adhesive. Additionally, and/or alternatively, the neutralizing composition acts to slow or decelerate the damaging effects of the stomal output, in some cases providing for increased or prolonged wear time of the ostomy appliance, which in turn provides both practical and economic advantages.

When preparing a base plate of an ostomy appliance to fit an individual user's stoma and body (skin surface), it often involves trimming or cutting (e.g. with special scissors) into correct shape and size an ostomy receiving opening in the base plate of the appliance. To avoid the thereby cut edge from gnawing on the stoma, and since adaptation of such opening in the base plate is difficult to make with a great deal of precision, the cutting/adaptation almost always leaves a small gap (distance) between an edge of the cut opening in the adhesive base plate and the user's stoma, when the appliance is applied around the stoma of the user. However, such gap does help to provide room for the stoma to 'work' (i.e. expand and contract), caused inter alia by peristaltic movements of the intestine; often, the stoma enlarges when delivering stomal output and shortens when not. This gap is also called the peristomal gap. Stomal output inevitably flows into the peristomal gap and will over time be able to propagate under the adhesive interface between the skin and the base plate.

Consequently, provision of an ostomy receiving opening and/or the peristomal gap also contributes to the risk of damage and degradation of the adhesive layer of the base plate followed potentially by skin irritation, maceration and/or other skin problems.

By providing a 'CME' including a release layer comprising a neutralizing component together with a base plate for an ostomy appliance, the neutralizing component can be directed into contact with the stomal output and into the peristomal gap. Both the user's skin and the adhesive layer on the base plate at, and adjacent to the peristomal gap, will thereby be protected from the damaging effects of the stomal output. While a small amount of neutralizing component may be forced into the collecting bag as stomal output leaves the stoma and passes through the stoma-receiving opening and into the collecting bag, the 'CME' of this disclosure is configured to ensure that a major portion of the neutralizing component is directed to flow particularly into the peristomal gap to interact with stomal output to neutralize its harmful components and avoid or delay degradation of the adhesive layer.

Experience shows that stomal output is able to flow substantially continuously or enter the collecting bag in bursts when exiting the stoma, depending among other factors on the type of stoma. If a user of an ostomy appliance is in an upright position, stomal output may flow continuously downwards due to gravity and thereby act to primarily 'wet' or 'soil' a portion of the base plate located below (beneath or under) the stoma when the appliance is worn. However, stomal output is known to also creep upwards to 'wet' or 'soil' a portion of the base plate located above (higher or over) the stoma when the appliance is worn.

Particularly, when stomal output enters the inside of a collecting bag in bursts, with a distal wall of the collecting bag pressed close to the stoma (e.g. due to the user's clothing, belt, trouser lining etc.), the stomal output is known to be able to spread all over a central portion of the base plate, including also the area above (higher/over) the stoma. For a user wearing a collecting bag with his/her clothes pushing the collecting bag's distal wall against the stoma, stomal output can be trapped in and fill a volume defined by the base plate, the distal wall of the collecting bag and an attachment between the base plate and the collecting bag (potentially a coupling arrangement between the base plate and the collecting bag). Thus, stomal output may not immediately or exclusively be forced downwards by gravity but can also be affected (by force(s) acting on it) to 'wet' or 'soil' an area of the collecting bag above (over) an inlet opening in the collecting bag and possibly also 'soil' the peristomal gap.

In conclusion, during normal use of an ostomy appliance, stomal output does not subject itself to an 'idealistic behaviour' of simply being forced by gravity to the 'bottom' of the collecting bag's reservoir volume. Instead, stomal output can (or be forced to) travel in any direction from the inlet opening of the collecting bag, including to areas/locations above (higher/over) the stoma. In some cases, stomal output can even be smeared against the walls (distal and/or proximal) of the collecting bag and further onto anywhere on a distal surface of the base plate and 'back' into the peristomal gap. Consequently, it is not easy to foresee where stomal output will 'end up' and present a problem. The present disclosure provides solutions which help avoid or prevent adhesive failure or at least reduce the impact of the stomal output's potentially damaging and detrimental effects on the user's skin surface, stoma and/or on the components of the ostomy appliance by offering a 'CME' which is configured to release a 'mitigating' neutralizing component.

From the above, it is understood that in conceiving the invention of the present disclosure, the inventors realized that the neutralizing component must not per se be provided close to, or in direct contact with, the stoma's surface, or directly onto the peristomal gap or skin surface for the neutralizing component to be able to provide its beneficial effects. Indeed, it was realized that the neutralizing component's effects are achievable inter alia by allowing the neutralizing component to be released in the peristomal gap, into an area of the collecting bag around the bag's inlet opening and/or on the base plate, such as on a central portion of the base plate, including on a distal surface of the base plate facing away from the skin of the user, when the ostomy appliance is worn. In some implementations, the 'CME' can be adapted to release the neutralizing component towards both a proximal surface of the base plate (facing the user's skin) and a distal surface of the base plate (facing or being exposed to the inside of the collecting volume of the collecting bag).

In embodiments, the 'CME' comprises an opening which is configured to receive the stoma and/or the stomal output from the user. In embodiments, the opening may be smaller or correspond to the through-going hole of the base plate. The size of the hole in the base plate and the opening of the 'CME' may be adapted by cutting prior to application to fit the stoma. In embodiments, the opening may be larger or correspond to the through-going hole of the base plate. In embodiments, the hole in the base plate may be cut larger prior to application and if the opening in the 'CME' is larger, cutting in the 'CME' may be unnecessary.

In embodiments, the 'CME' is sealed along the inner edge, being the edge surrounding the opening. Such sealing may prevent the content of the 'CME' to flow and escape the 'CME' during storage. In embodiments, the 'CME' comprises means for breaking the sealing along the opening, so the neutralizing component can be released during use. In embodiments, the sealing comprises a label or string, that when removed from the 'CME', tears the sealed edge open.

In embodiments, the 'CME' is open along the inner edge, thereby providing a ready-to-use product.

The 'CME' is provided with a cover layer on the first surface of the element. In embodiments, the first surface is on the distal side of the 'CME'. The cover layer facilitates that the 'CME' does not stick to the inside of the collecting bag as well as the cover layer may be able to control the release of the neutralizing component.

In embodiments, the second surface complementary-material element is provided with a second cover layer. In embodiments, the second surface is on the proximal side of the 'CME'. In embodiments, the first and the second cover layer are sealed together along an outer periphery to define a closed envelope containing the release layer. In embodiments, the sealing along the outer edge is not entirely fluid tight but enables pockets of gas inside the envelope to escape during the sealing process.

In embodiments, the second surface of the complementary-material element is configured to be attached to a base plate of an ostomy appliance. The surface may comprise an adhesive material. The adhesive material may for example be a continuous adhesive layer, a pattern-coated adhesive layer or the adhesive material may be arranged in one or more discrete areas. In embodiments, the adhesive material is arranged in concentric circles around a hole for accommodating a stoma. In embodiments, a plurality of individual adhesive areas is provided on an external surface of the 'CME'. In embodiments, the complementary-material element further comprises at least one release liner. The release liner may cover the adhesive material and is removed before use.

In embodiments, the first cover layer is water impermeable or has a low permeability to water. This facilitates that the release layer will not unintended leak through the first cover layer from the 'CME'. I case the release layer is viscous or comprises volatile components, an impermeable cover layer provides better storage stability. In embodiments, the first cover may comprise a polymer film such as a polyurethane film, a polyethylene film, a PVDC (polyvinyl dichloride) film or laminates comprising these.

In embodiments, the first cover layer is water permeable. This allows the moisture from the output from the stoma to enter the release layer over a larger surface thereby achieving a faster release of the neutralizing component. In embodiments, the cover layer is designed to provide a controlled release of the neutralizing component. In embodiments, the first cover layer may be a non-woven or a net. In embodiments, the first cover layer is an impermeable film provided with a plurality of holes.

In embodiments, the second cover layer is water impermeable or has a low permeability to water. In embodiments, the second cover may comprise a polymer film such as a polyurethane film, a polyethylene film, a PVDC (polyvinyl dichloride) film or laminates comprising these.

In embodiments, the second cover layer is water permeable. In embodiments, the cover layer may be a non-woven or a net. In embodiments, the second cover layer is an impermeable film provided with a plurality of holes.

In embodiments, the first cover layer and the second cover layer are made from the same material.

In embodiments, the cover layer is transparent, translucent or opaque, enabling that the content of neutralizing component can be inspected from the outside. In embodiments, the cover layer is non-transparent in order to visually conceal any output from the stoma entering the envelope.

In embodiments, at least one surface of the 'CME' is embossed to show a pattern. In embodiments, the embossment is provided by attaching the first and the second layer together in a pattern of lines or points.

In embodiments, a foam layer is inserted between the release layer and the first cover layer. Such foam layer may be wetted by the output and thereby exposing the release layer to the moisture from the output over the first surface of the 'CME'.

The complementary-material element may have any suitable shape. In embodiments, the element is disc shaped, optionally with a central through-going hole for accommodating the stoma. In embodiments, the 'CME' is provided without a hole, so the user can adapt the hole to his or her stoma. In embodiments, it has a substantially flat, sheet-like configuration. In embodiments, the complementary-material element has an outer periphery being circular, oval or droplet shaped.

In embodiments, the complementary-material element is provided with a cut-out section extending radially inwards from an edge of the element. Such cut-out section facilitates easy placement of the element around the stoma.

In embodiments, the release layer is provided as a matrix structure. In embodiments, the release layer can include more than one neutralizing component. In embodiments, a neutralizing component can include more than one kind of neutralizing component (e.g. directed towards neutralizing different substances of the stomal output). In some implementations, the helpful effect(s) presented by one neutralizing component and/or one neutralizing component can be amplified by the presence of another kind of neutralizing component and/or neutralizing component to provide even better results in terms of preventing or at least reducing the prevalence of adhesive failures, skin maceration, contact dermatitis, leakage incidents etc.

In embodiments, a matrix structure of the release layer comprises a neutralizing component incorporated therein. The neutralizing component can be dissolved in the matrix or it can be dispersed as particles in the matrix. In embodiments, the matrix comprises coated neutralizing substance particles. The matrix serves as a carrier of the neutralizing component and is configured to release the neutralizing component. In embodiments, the matrix is configured to release the neutralizing component when the matrix is subjected or exposed to certain conditions. Such conditions may for example be in the presence of stomal output containing moisture or in the presence of moisture from other sources, e.g. sweat from the user's body.

Inside the collecting volume of a collecting bag, humidity will quickly reach close to 100% humidity, so the presence of moisture is substantial. In embodiments, the release of neutralizing component initiates shortly after applying the ostomy appliance on the user, due to the high relative humidity in the collecting bag.

In embodiments, the matrix comprises one or more of a gel, foam, film layer or paper or a coating. Such coating may for example be solid or powder coating. In embodiments, the matrix and the neutralizing component form a colloidal solution such as a sol. One suitable example of a matrix comprises an adhesive comprising 50% w/w polyisobutylene (PIB) and 25% w/w CMC and 25% w/w pectin.

In embodiments, a matrix in the form of a water-soluble film comprises a PVOH based thermoplastic film, such as a Monosol® 7031 film from kurakay WS Film Division™, Portage, Ind., United States.

In embodiments, the matrix is configured to be soluble in water (moisture) or a component of the stomal output. It can be slowly soluble, by slowly is herein meant that the matrix will not degrade instantly, but slowly dissolve during wear of the base plate. In embodiments, when output from the stoma is floating over the release layer, the matrix will dissolve, and the neutralizing component will be washed away, and at least a part of the neutralizing component will enter into the peristomal gap.

In embodiments, the matrix is configured to absorb moisture and turn into a gel like material when wetted by moisture uptake. The gel can be delivered in an initial dry form and configured to subsequently swell into a gel when brought into contact with moisture. The gel can be slowly soluble in water or in a component of the output (moisture) or it can be insoluble, but able to release the neutralizing component when exposed to the stomal output and/or moisture. Examples of suitable materials for the matrix may be polyethylene glycol (PEG), polyvinyl alcohol (PVA), polyvinyl pyrrolidone (PVP), ethylene vinyl acetate (EVA) based matrix and hydrocolloids such as CMC or gelatine.

In embodiments, the matrix comprises polysaccharides and/or hydrocolloids. The polysaccharides or hydrocolloids can be configured to dissolve or hydrate when exposed to output, thereby releasing the neutralizing component.

In embodiments, the matrix comprises protein.

In embodiments, the matrix is substantially non-adhesive. By non-adhesive is to be understood that the matrix is not adhesive (does not stick). In some implementations, however, the matrix is configured to, under certain circumstances, become slightly sticky when wetted. A non-adhesive matrix will be less prone to sticking to the distal wall of the bag. In embodiments, the matrix may be sticky, but the presence of a first cover layer may prevent the matrix to stick to the distal wall of the bag.

In one aspect, the disclosure relates to a kit of parts comprising a complementary-material element as disclosed herein and a base plate for an ostomy appliance. The base plate comprises an adhesive layer provided on a first surface of a backing layer. Optionally, the base plate comprises a release liner provided on the adhesive first surface of the backing layer.

In embodiments, a body waste collecting bag attached to the second surface of the backing layer of the base plate.

In embodiments, at least a portion of the element extends radially to cover at part of an inner proximal wall of a collecting bag. This facilitate a larger area of release layer as well as the thickness of the 'CME' can be reduced, thereby enhancing the flexibility of the appliance.

In embodiments, a first coupling half provided on the second surface of the backing layer of the base plate and a body waste collecting bag having a second coupling half provided around an inlet opening of the collecting bag.

In embodiments, the base plate comprises second attachment means for attachment to the complementary-material element.

In embodiments, the complementary-material element is/are attachable to the base plate by a user or a health care professional. Alternatively, the element is attached to the base plate at manufacture and delivered to the user in an attached configuration. Such attachment inter alia allows for easier adaptation of a stoma-receiving opening in the base plate when customization of the size and shape of the opening to the user's stoma is required. In embodiments, the 'CME' is attached to the base plate by welding, lamination, hot melt adhesive or double faced adhesive tape.

In embodiments, the kit of parts further comprises a body waste collecting bag attached to the second surface of the backing layer of the base plate. In these embodiments, the collecting bag is already attached to the base plate at manufacture and may be understood as a one-piece ostomy appliance, as is commonly understood in the ostomy appliance area. Such embodiments of a one-piece ostomy appliance of the disclosure provide one-piece appliances which may have prolonged wear time, due to the combination with the attached or attachable complementary-material element. The collecting bag can thus be detachably or permanently attachable to the base plate via a coupling arrangement.

In embodiments, a first coupling half is provided on the second surface of the backing layer of the base plate. The body waste collecting bag includes a second coupling half provided around an inlet opening of the collecting bag. This provides for the complementary-material element of the disclosure to also be used with and improve the life- or wear time also of a two-piece ostomy appliance, also commonly understood in the area.

In embodiments, the base plate comprises second attachment means for attachment to the complementary-material element. In these embodiments, the element comprises first attachment means to engage or attach to the second attachment means of the base plate.

In embodiments, the complementary-material element is configured as a ring-shaped element or as a disc-shaped element. Thereby, the 'CME' is intuitive and easily handled by the user or health care professional. This is particularly, but not exclusively, advantageous when the 'CME' is combined with and attached to a base plate of an ostomy appliance by the user or health care professional (i.e. it is not attached to the base plate at manufacture) before the base plate is being applied to the skin of the user.

In embodiments, the 'CME' comprises an opening which is configured to receive the stoma and/or the stomal output from the user. In some implementations, the 'CME' is a ring-shaped element comprising a central opening, wherein attachment of the 'CME' to the base plate becomes particularly intuitive, because the ring-shaped element (the 'CME') is configured to align with a stoma-receiving opening in the base plate and to be customized to fit well with the size and shape of an individual stoma.

In embodiments, the collecting bag comprises a second half of a coupling interface that is configured to couple with a first half of the coupling interface on the base plate to attach the stomal collecting bag to the base plate.

In embodiments, a distal surface of the base plate includes a first half of a coupling interface for coupling the base plate to a collecting bag. In one embodiment, the coupling half is a flange adapted to provide a surface for attaching another coupling half in the form of an adhesive flange provided on the collecting bag. In embodiments, the first half of the coupling interface is configured as a flexible, planar annular flange optionally comprising an adhesive. The first coupling half is adapted to couple with a second coupling half provided around an inlet opening of the collecting bag by means of an adhesive. The adhesive coupling may provide a releasable or a permanent adhesive coupling engagement between the components.

In embodiments, the coupling half is an annular ring comprising an upstanding flange protruding from the distal surface perpendicular thereto for attaching another coupling half in the form of a coupling ring provided on the collecting bag. In one embodiment, a first coupling half is attached to a distal surface of the base plate. In embodiments, the first coupling half is attached to the distal surface by an adhesive or by welding, but other ways of attaching are acceptable. Other types of suitable coupling arrangements are widely available within the ostomy care field.

By neutralizing component is herein meant a neutralizing substance capable of neutralizing or at least minimizing the level of skin- or adhesive-aggressiveness of stomal output.

In embodiments, the neutralizing component comprises a clay, such as organophilic clay, for example bentonite or synthetic clay such as laponite. Examples of such clays are disclosed in EP 1 140 009.

In embodiments, the neutralizing component comprises potato-derived inhibitors or protease inhibitors. Examples of potato-derived inhibitors such as potato protein are disclosed in EP 1 736 136.

In embodiments, the neutralizing component can include an adhesive. In other embodiments, the neutralizing component comprises a powder. In other embodiments, the neutralizing component comprises a liquid. In other embodiments, the neutralizing component comprises a gel. In other embodiments, the neutralizing component comprises a plurality of pellets. In yet other embodiments, the neutralizing component comprises a combination of any one or more of an adhesive, a powder, a liquid, a gel and/or a plurality of pellets. These options each provides one or more different advantages such as including, but not limited to, manipulability, shelf life, suitability for different kinds of stomal output (colostomy output tends to be much more solid than ileo- and urostomy output), processing characteristics during manufacture and others. By selectively applying these options, individually or in combination, to meet particular requirements of a target ostomy/ostomist group, the suitability of the ostomy appliance and the improvement in reduction or elimination of the problems discussed above, including reducing the risk of leakage, can be significantly improved.

Particularly, in embodiments wherein the neutralizing component comprises an adhesive, suitable materials include adhesives, such as, but not limited to, adhesive pastes. Suitable materials for a paste-type adhesive comprise adhesives of the types disclosed in WO2010/069334. Other types of adhesive pastes are also acceptable.

DETAILED DESCRIPTION OF THE DRAWINGS

FIG. 1 is a schematic cross-sectional side view of one embodiment of an ostomy appliance 10 including a complementary-material element 60, a base plate 20 to which the complementary-material element 60 is attached, and a stomal output collecting bag 50 coupled to the base plate at location 100 and configured to collect stomal output coming out of the user's stoma 110. The base plate 20 is adhesively attached to the skin surface S surrounding the stoma 110. Also visible is an area or zone immediately surrounding the stoma 110, the area or zone designated the peristomal gap 120. The embodiment of FIG. 1 further illustrates a first cover layer 80 located on a first surface 130 of the complementary-material element 60. On a second surface of the complementary-material element is provided a second cover layer 140. The second cover layer 140 is attached to the central portion of the backing layer 40 of the base plate 20.

Figure 7:
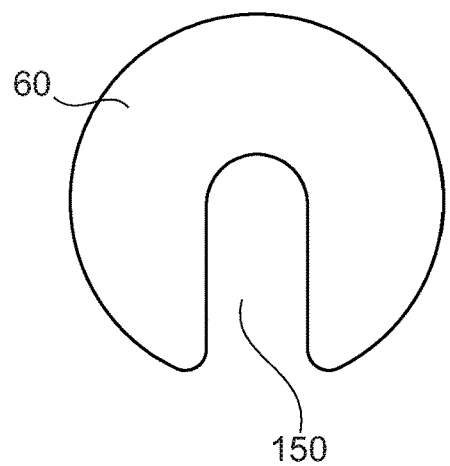
FIG. 7 is a top view of an embodiment of a complementary-material element with a cut-out section.

FIG. 2 is a schematic view, seen from above, of an embodiment of a complementary-element 60. The complementary-material element is her shown as symmetric disc shaped, but may come in other shapes, for example as a disc with a cut-out 150 as shown in FIG. 7. In FIG. 7 is shown the cut-out 150 facilitates easy placement around a stoma. In embodiments, the complementary-material element may have an asymmetrical shape. The complementary-material element may be provided with a through-going hole for accommodating a stoma.

FIG. 3 show a cross-sectional perspective view of a complementary-material element 60, cut along the A-A line shown in FIG. 2. The complementary-material element 60 comprises a neutralizing component matrix 70. On a first surface 130 of the complementary-material element is provided a first cover layer and on a second surface 140 of the complementary-material element is provided a second cover layer 90. The first cover layer 80 and the second cover layer 90 are sealed along an outer periphery 160 of the complementary-material element to produce a closed envelope containing the neutralizing component matrix 70. The second cover layer 90 may be provided with an adhesive material (not shown) for attachment to a base plate.

Figure 5:
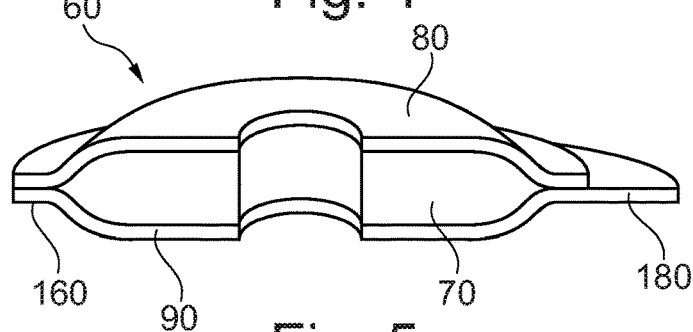
FIG. 5 is a schematic cross-sectional view of an embodiment of a complementary-material element with a tab member.

In FIG. 4 is shown a cross-sectional view of a complementary-material element 60 wrapped in a first cover layer 80 and a second cover layer 90 sealed along the outer periphery 160. At the centre portion 170, the neutralizing component matrix 70 is absent or substantially absent, leaving the first cover 80 and the second cover layer 90 next to each other's or solely separated by a neglectible amount of neutralizing component matrix 70. Before use, a through-going hole is cut in the centre portion to adapt the complementary-material element 60 to fit around a stoma. In FIG. 5 is shown a cross-sectional perspective view of an embodiment where an outer edge portion of the first cover layer 80 and/or the second cover layer 90 is elongated radially into a tab portion 180, thereby facilitating easy removal of the complementary-material element 60 when the tab portion 180 is pulled away from the base plate.

Figure 6:
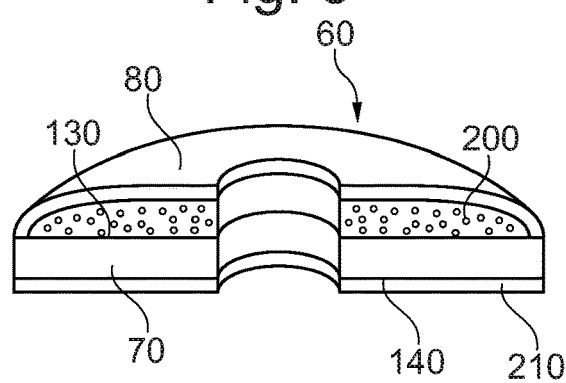
FIG. 6 is a schematic cross-sectional perspective view of an embodiment of a complementary-material element with a foam layer.

In FIG. 6 is shown a cross-sectional perspective view of an embodiment comprising a neutralizing component matrix 70, the neutralizing component matrix 70 being provided with a foam layer 200 inserted between the first surface 130 of the neutralizing component matrix 70 and the first cover layer 80. The foam layer 200 facilitates distribution of output from the stoma to reach the entire first surface 80 of the release layer 70, thereby providing faster release of neutralizing component from the neutralizing component matrix 70. The first cover layer 80 may prevent the complementary-material element 60 from sticking to the collecting bag 50. The second surface 140 of the complementary-material element 60 is provided with an adhesive material 210 for attaching the complementary-material element 60 to a base plate.

Figure 8:
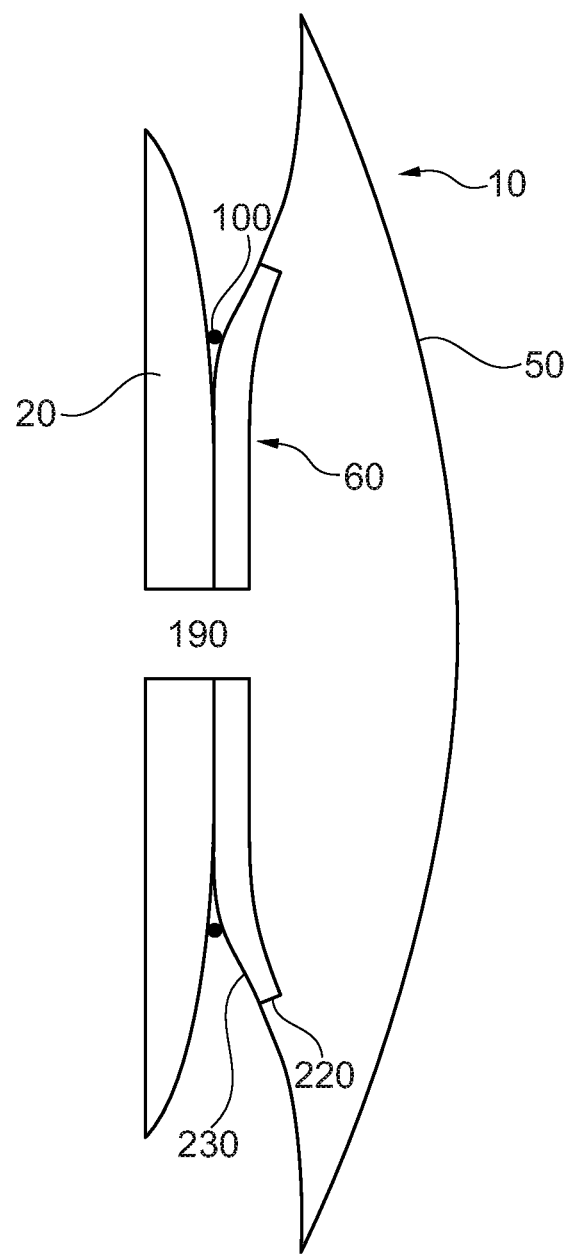
FIG. 8 is a cross-sectional view of an embodiment of an appliance with a complementary-material element extending over the inner proximal wall of the collecting bag.

FIG. 8 shows a cross-sectional view of an embodiment of an appliance with a complementary-material element 60 attached. The complementary-material element extends radially from the through-going hole 190 to an outer edge portion. The complementary-material element extends over the central portion of the base plate 20 and further over the location 100 for attachment of the collecting bag 50 to cover a portion of the inside proximal wall 230 of the collecting bag 50. The complementary-material element may be attached to the inside proximal wall or it may only be attached to the base plate. The attachment to the base plate may be over a continuous area or it may be in discrete points or lines. In embodiments, the complementary-material element may be attached by welding, lamination or adhesive.

FIGS. 9 and 10 show embodiments of appliances with an asymmetrical complementary-material element attached to the base plate. In FIG. 9, the complementary-material element 60 extend further towards the top of the collecting bag than it extends towards the bottom of the collecting bag. The extended portion 220 may be attached to the distal inner wall 240 of the collecting bag 50. In FIG. 10, the complementary-material element 60 extends further towards the bottom of the collecting bag than it does towards the top of the collecting bag. The extended part 220 may be unattached to the inner proximal wall 230 of the collecting bag 50.

Figure 11:
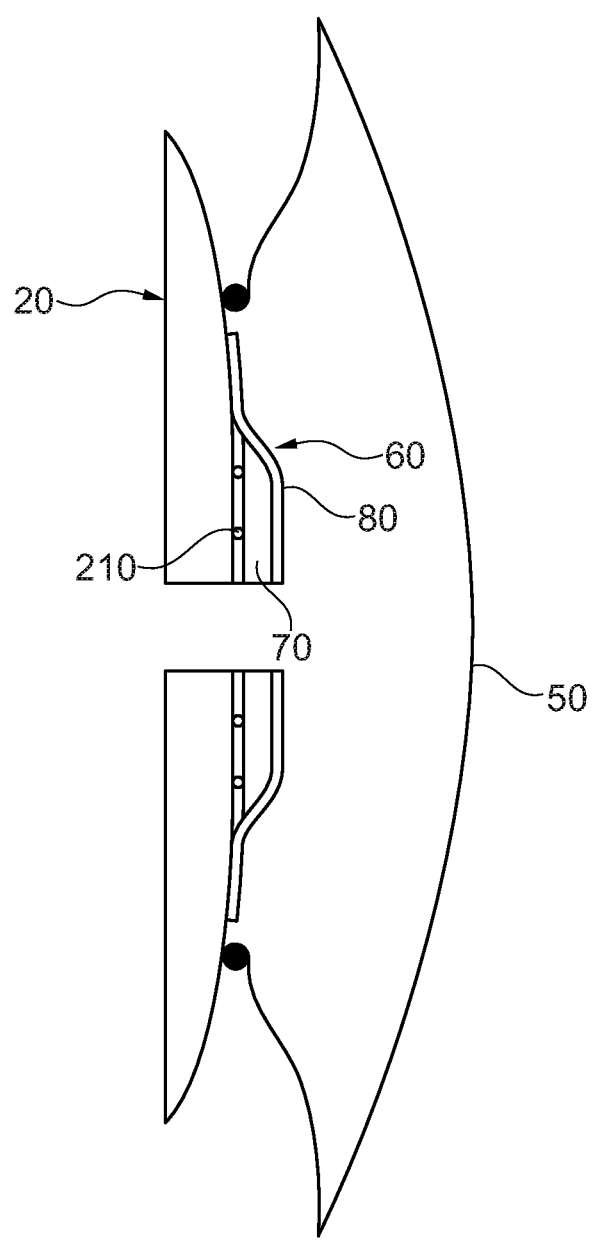
FIG. 11 is a cross-sectional view of an embodiment of an appliance with a complementary-material element where the element is attached in points.

In FIG. 11, the complementary-material element 60 is attached to the base plate 20 in discrete points 210. This construction facilitates more flexibility of the combined base plate and complementary-material element when the base plate is bended during application and use.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of body side members for ostomy appliances as discussed herein. Therefore, it is intended that this invention be limited only by the claims and the equivalents thereof.

The invention claimed is:

1. An ostomy appliance comprising:
   a base plate attachable to skin of a user around a stoma; and
   a complementary-material element comprising a first surface having a first cover layer and a second surface attachable to the base plate, where the complementary-material element comprises a release layer between the first surface and the second surface;
   wherein the base plate has a through-hole for receiving the stoma and the complementary-material element has a cut-out for placement relative to the stoma;
   wherein a peristomal gap is formed between the stoma and the through-hole of the base plate and the cut-out of the complementary-material element when the base plate and the complementary-material element are placed over the stoma during use;
   wherein the release layer comprises a neutralizing component and at least one of moisture contact and stomal output contact with the release layer causes the neutralizing component to be released from the complementary-material element such that the neutralizing component is released into the peristomal gap to neutralize the stomal output and protect the skin around the stoma.

2. The ostomy appliance of claim 1, wherein the complementary-material element is sealed around a periphery of the cut-out to form an envelope to contain and prevent release of the neutralizing component from the complementary-material element during storage.

3. The ostomy appliance of claim 2, wherein the complementary-material element is sealed around a periphery of the cut-out by one of a removable label and a string, where each of the label and the string is adapted to be removed to expose the neutralizing component at the periphery of the cut-out.

4. The ostomy appliance of claim 1, wherein the second surface is provided with a second cover layer.

5. The ostomy appliance of claim 4, wherein the first cover layer and the second cover layer are sealed together along an outer periphery of the first cover layer and the second cover layer to prevent release of the neutralizing component from the outer periphery.

6. The ostomy appliance of claim 1, wherein the complementary-material element is circular and the cut-out is a round opening adapted to receive the stoma, and a peripheral edge of the round opening is uncovered to allow release of the neutralizing component.

7. The ostomy appliance of claim 1, wherein the first cover layer is water impermeable.

8. The ostomy appliance of claim 1, wherein the first cover layer is water permeable.

9. The ostomy appliance of claim 1, wherein the first cover layer is transparent and adapted to allow a user to visually inspect the neutralizing component.

10. The ostomy appliance of claim 1, wherein the release layer comprises a matrix structure containing the neutralizing component.

11. The ostomy appliance of claim 1, wherein the second surface comprises an adhesive material.

12. The ostomy appliance of claim 1, further comprising:
a foam layer inserted between the release layer and the first cover layer.

13. The ostomy appliance of claim 1, wherein the release layer comprises a matrix structure containing the neutralizing component and the matrix structure is soluble in water.

14. The ostomy appliance of claim 1, wherein the release layer comprises a matrix structure containing the neutralizing component and the matrix structure dissolves in response to the stomal output.

15. The ostomy appliance of claim 1, wherein the neutralizing component flows from and is released from the complementary-material element and into the peristomal gap in response to a presence of moisture from sweat or humidity.

* * * * *